United States Patent [19]
Serrano et al.

[11] Patent Number: 6,049,015
[45] Date of Patent: Apr. 11, 2000

[54] METHOD FOR C-ALKYLATING HYDROXYLATED AROMATIC COMPOUNDS

[75] Inventors: Cécile Serrano, Villeurbanne; Michel Dury, Lyons; Jean-Roger Desmurs, St Symphorien d'Ozon; Paul Cruciani, Lyons, all of France

[73] Assignee: Rhodia Chimie, Courbevoie Cedex, France

[21] Appl. No.: 09/066,447

[22] PCT Filed: Oct. 31, 1996

[86] PCT No.: PCT/FR96/01722

§ 371 Date: Aug. 31, 1998

§ 102(e) Date: Aug. 31, 1998

[87] PCT Pub. No.: WO97/16402

PCT Pub. Date: May 9, 1997

[30] Foreign Application Priority Data

Oct. 31, 1995 [FR] France .................................... 95 13110

[51] Int. Cl.⁷ .................................................... C07C 37/14
[52] U.S. Cl. ............................ 568/788; 568/785; 568/793
[58] Field of Search ..................................... 568/707, 708, 568/716, 717, 727, 763, 766, 804, 785, 788, 793

[56] References Cited

U.S. PATENT DOCUMENTS

| | | | |
|---|---|---|---|
| 3,373,210 | 3/1968 | Nishio et al. | 260/624 |
| 4,461,916 | 7/1984 | Alfs et al. | 568/788 |

FOREIGN PATENT DOCUMENTS

| | | |
|---|---|---|
| 1160491 | 8/1969 | United Kingdom. |
| 1 469 896 | 6/1977 | United Kingdom. |

OTHER PUBLICATIONS

Chemical Abstracts, vol. 62, No. 6, Mar. 15, 1965, Columbus, Ohio, Abstract No. 6434a, col. 6434, XP002008358.

Collection of Czechoslovak Chemical Communications, vol. 29, No. 2, Feb. 1964, Prague, CS, pp. 381–389, XP002008357, J. Pospisil et al, "Alkylierung von Hydrochinon mit Isobutylen und Diisobutylen".

Chemical Abstracts, vol. 119, No. 13, Sep. 27, 1993, Columbus, Ohio, Abstract No. 138864s, p. 838; XP002008359.

Collection of Dzechoslovak Chemical Communications, vol. 31, No. 1, 1966, Prague, CS, pp. 98–105, XP002024507, J. Popisil et al, Antioxydantien und Stabilisatoren X. Bermerkung zur Darstellung einiger Hydrochinon–alkylderivate.

Journal of the American Chemical Society, vol. 64, No. 4, Apr. 1942, Washington, D.C. pp. 937–940, P002024508, P.F. Oesper et al, "The reduction of dipole moment by steric hindrance in di–t–butylhydroquinone and its dimethyl ether".

Collection of Czechoslovak Chemical Communications, vol. 34, No. 7, 1969, Prague CS, pp. 1991–2001, XP002024509, I. Buben et al, "Oxidation of pyrocatechol. VII. Oxidation of 4–tert–alkylpryocatechols and 2–tert–alkylhydroquinones by oxygen in an alkaline medium".

Collection of Czechoslovak Chemical Communications, vol. 30, No. 4, 1965, Prague, CS pp. 1092–1103, XP002024510, J. Popisil et al, "Antioxydantien und Stabilisatoren V. Darstellung von tert–Butyl–und tert–Octylderiaten des Brenzcatechins", see p. 1100–1103, table 1.

Chemical Abstracts, vol. 117, No. 9, Aug. 31, 1992, Columbus, Ohio, Abstract No. 89901z, S.D. Kim et al, "A study on the tert–butylation of hydroquinone", see p. 743, XP002024511, see abstract & Hwahak Koghak, vol. 30, No. 1, 1992, pp. 18–25.

Chemical Abstracts, vol. 67, No. 5, Jul. 31, 1967, Columbus, Ohio. Abstract No. 21664, p. 2049, XP002024512, see abstract & * CS 119 828 A (J. Popisil et al).

*Primary Examiner*—Sreeni Padmanabhan
*Attorney, Agent, or Firm*—Burns, Doane, Swecker & Mathis, L.L.P.

[57] ABSTRACT

A method for C-alkylating a hydroxylated aromatic compound having at least one hydrogen atom in the ortho or para position relative to the hydroxyl grouping, wherein the aromatic compound is exposed to a proton acid and a compound causing the formation of a carbo-cation in the presence of the acid, and the reaction is performed in the presence of a solvent consisting of a water-alcohol pair.

18 Claims, No Drawings

METHOD FOR C-ALKYLATING HYDROXYLATED AROMATIC COMPOUNDS

This is the U.S. National Stage Application of PCT/FR96/01722 filed Oct. 31, 1996 now WO97/16402 published May 9, 1997.

The present invention relates to a novel process for the C-alkylation of hydroxylated aromatic compounds having at least one hydrogen atom ortho or para to the hydroxyl group. The invention relates in particular to the preparation of 2,5-di-tert-octyl-hydroquinone.

The synthesis of 2,5-di-tert-octylhydroquinone by reaction between hydroquinone and diisobutylene, and more generally the synthesis of hydroxylated aromatic compounds having at least one hydrogen atom ortho or para to the hydroxyl group, has formed the subject of many reaction condition variants in order to improve the yield.

CS patent No. 111,292 proposes the alkylation of 2-methylhydroquinone, 2-tert-butylhydroquinone and 2-tert-octylhydroquinone by diisobutylene with catalysis by concentrated sulphuric acid in the presence of inert solvents (chloroform) or reactive solvents such as ice-cold acetic acid or excess diisobutylene. The yields listed are of the order of 35%. See also in the same respect J. Pospisil and L. Taimr in Collect. Czech. Chem. Commun. 29 (1964), 381-5.

Patent GB-A-1,469,896 describes a process for the synthesis of a hydroxy-(1,1,3,3-tetramethylbutyl)-benzene by reaction between a hydroxybenzene having one or more hydroxyl groups and being optionally substituted, in particular hydroquinone, and a 2,4,4-trimethylpentene, i.e. one of its α-diisobutylene and β-diisobutylene isomers, or a mixture of the two, in the presence of highly concentrated sulphuric acid and ethylene glycol. As regards that patent, the expression highly concentrated sulphuric acid means a concentration in water of greater than 90% and preferably of about 95±3%. The yield listed is of the order of 60% starting from hydroquinone.

CS patent 273,290 proposes to prepare 2,5-bis-(1,1,3,3-tetramethylbutyl)hydroquinone by alkylation of hydroquinone by diisobutylene with sulphuric acid as catalyst, in a mixture of methanol and aliphatic hydrocarbons. The yield listed is of the order of 65%.

Lastly, patent U.S. Pat. No. 3,373,210 proposes to carry out the alkylation reaction in the presence of methanol and with sulphuric acid as catalyst, for a listed yield of 25%.

In practice, it often turns out to be difficult to obtain the yields listed in these documents. In addition, non-negligible polymerization problems are encountered.

There is thus still a need for a synthetic process which leads simply and reproducibly to advantageous yields, and which furthermore minimizes the risks of polymerization.

The object of the invention is to propose such a process.

The subject of the present invention is thus a process for the C-alkylation of a hydroxylated aromatic compound having at least one hydrogen atom ortho or para to the hydroxyl group, in which process this aromatic compound is placed in the presence of a strong protonic acid and of a compound leading to the formation of a carbocation in the presence of the acid, the reaction being carried out in the presence of a solvent formed of a water/alcohol couple.

The term "aromatic" is taken here in its classical notion as defined in the book by Jerry March, Advanced Organic Chemistry, 4th Edition, published by John Wiley & Sons, 1992.

The starting aromatic compound will be referred to hereinbelow as hydroxybenzene. It can in particular have the formula:

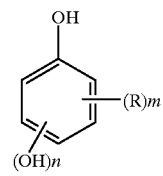

(1)

in which
n=0 to 4, in particular 0 or 1, preferably 1
m=0 to 4, preferably 0 or 1
with n+m≦4
R is chosen from the group consisting of:
   linear or branched C1 to C30, in particular C1 to C6, preferably C1 to C4, alkyl, which can optionally have one or more hetero atoms (Cl, Br, O, N, etc.) for example $CF_3$,
   one or more alkyls connected to the aromatic ring by a hetero atom (N, S, O, etc.), the alkyl corresponding to the above definition, for example an alkoxy group, in particular a C1 to C4 and preferably a C1 to C2 alkoxy, for example also methylsulphide or dimethylamine,
   a halogen atom, preferably Cl or Br.

They can also be compounds with a heteroaromatic ring, for example hydroxypyridine, or bicyclic aromatic compounds.

In particular, in the case of formula (1), 2 groups R placed on 2 adjacent carbon atoms can form, together with the carbon atoms which bear them, 1 optionally substituted aromatic ring.

The expression formation of carbocation should be understood to mean the formation of carbocation with or without the possibility of rearrangement. The compounds liable to form a carbocation in the presence of the acid are preferably selected from the group consisting of:

at least C3, in particular C3 to C30, olefinic compounds;
secondary and tertiary alcohols; and
ethers and amines having at least one secondary or tertiary group; these can be, in particular, symmetrical or asymmetrical ethers or amines having at least one secondary or tertiary alkyl group connected to the oxygen.

The solvent according to the invention is formed of an alcohol/water couple in which the alcohol is preferably a lower alcohol chosen, in particular, from the group consisting of methanol, ethanol, isopropanol, cyclohexanol and ethylene glycol, or a mixture of at least two of these. Methanol is the preferred alcohol.

In accordance with the invention, a solvent formed of an alcohol and water must be present. Water and alcohol forming this couple will generally be added when the reaction is carried out. However, in certain cases, when ethers or alcohols will be used as a source of carbocation, water and/or alcohol of the solvent may be generated in situ partly or totally from the ether or alcohol reactants.

The water/alcohol ratio (as a % by volume) in the solvent is preferably between 40/60 and 60/40. A 50/50 ratio is particularly suitable, especially when the alcohol is methanol. The water + alcohol solvent will preferably be used in a proportion of from 1 to 10 ml, more preferably from 1 to 5 ml, per 1 g of acid. According to an advantageous mode of the invention, about 1 ml of water and 1 ml of alcohol, in particular methanol, may be used per 1 g of acid.

The water + alcohol/acid ratio may generally be between 1/0.1 and 1/10, preferably between 1/0.5 and 1/5, expressed as volume (ml)/mass (g).

The acid may be used in a proportion of from 0.05 to 4 equivalents per 1 equivalent of hydroxybenzene.

The olefinic compound can be a linear or branched unsaturated aliphatic hydrocarbon containing at least one double bond, preferably in the α position.

The number of carbon atoms can be very variable. It is preferably between 3 and 30 carbon atoms.

The olefinic compound can also be an unsaturated, monocyclic or carbocyclic hydrocarbon or a polycyclic hydrocarbon comprising at least two carbocycles, it being possible for one or more hetero atoms to be present in the ring and at least one endocyclic or exocyclic unsaturation being present.

1 or 2 unsaturations may be present in the ring. It should be noted that the double bond can also be exocyclic.

The olefinic compound can also be a terpenic compound.

When it is a monocyclic hydrocarbon, the number of carbon atoms in the ring can vary widely from 4 to 20 carbon atoms, but is preferably 5 or 6 carbon atoms.

The hydrocarbon can also be polycyclic, preferably bicyclic, which means that at least two rings have two carbon atoms in common.

In the case of polycyclic hydrocarbons, the carbon condensation of each ring is lower, generally from 3 to 8, and is preferably equal to 5 or 6 carbon atoms.

It should be noted that any ring can bear one or more substituents.

The number of substituents present on the ring depends on the carbon condensation of the ring and on the presence or absence of unsaturation on the ring.

The maximum number of substituents which can be borne by a ring is easily determined by a person skilled in the art.

Generally, the number of substituents present on a ring is from 1 to 3, preferably 1 or 2.

As regards the nature of the substituents, the examples of substituents given for R are suitable, but this list is not limiting in nature. Alkyl groups are usually the preferred substituents.

The olefinic compounds will be chosen, as is known per se, on the basis of the desired final product.

In an entirely preferred manner, the object of the process according to the invention will, in particular, be to produce 2,5-di-tert-octylhydroquinone or 2,5-bis(1,1,3,3-tetramethylbutyl)hydroquinone. In practice, hydroquinone will be chosen as hydroxybenzene and diisobutylene, i.e. α-diisobutylene or β-diisobutylene or a mixture of both, will be chosen as olefinic compound. The reaction, which should lead to the grafting of two octyl groups onto the hydroquinone, is generally carried out in the presence of at least 2 mol of diisobutylene per 1 mol of hydroquinone. It goes without saying that for the grafting of two alkyl groups per hydroxybenzene molecule at least 2 mol of olefins need to be used per 1 mol of hydroxybenzene, unless the reaction is carried out twice. For the grafting of only one alkyl group, one mole of olefin will preferably be sufficient per 1 mol of hydroxybenzene.

As additional examples, in accordance with the invention, it is also possible to produce, starting from the aromatic compound and a suitable olefinic compound, the following final products:

di-tert-butyl-4-nonylphenol (olefin=linear C9 alkene; aromatic compound=di-tert-butyl-4-phenol)

ortho-(methylcyclohexyl)-phenol (olefin=1-methyl-1-cyclohexene; aromatic compound=phenol)

diamylhydroquinone (olefin=branched C5 alkene; aromatic compound=hydroquinone)

camphenylphenol (olefinic compound=camphene; aromatic compound=phenol).

A certain number of substituents for the initial hydroxybenzene and a certain number of olefinic compounds which can be used have been mentioned. However, it goes without saying that the invention is not limited thereto and that the process according to the invention can be applied to other substituents and olefinic compounds known in the prior art.

The source carbocation compound will preferably be used in a proportion of from 1 to 10 equivalents, preferably from 2 to 5 equivalents, per 1 equivalent of hydroxybenzene.

As regards the secondary or tertiary groups of the alcohols, ethers and amines, these can, in particular, be groups having from 3 to 30 carbon atoms, optionally with rings and hetero atoms, in particular as has been stated with regard to the groups of the olefinic compounds.

Mention may be made of tert-butanol as tertiary alcohol, methyl tert-butyl ether (MTBE) as ether and N-methyl-tert-butylamine as amine.

In the present invention, the terms strong protonic or protic acid denote an acid having a pKa in water of less than −0.1 and preferably less than −1.0.

The pKa is defined as the ionic dissociation constant of the acid/base couple, when water is used as solvent.

The strong protonic acids according to the invention are preferably chosen from sulphuric acid and more preferably sulphonic acids, in particular halosulphonic acids such as fluorosulphonic acid, chlorosulphonic acid or trifluoromethanesulphonic acid; methanesulphonic acid, ethanesulphonic acid, ethanedisulphonic acid, benzenesulphonic acid, benzenedisulphonic acid, toluenesulphonic acid, naphthalenesulphonic acid, naphthalenedisulphonic acid, camphorsulphonic acid, triflic acid and xylenesulphonic acid.

Benzenesulphonic acid will mainly be preferred, as well as triflic acid, methanesulphonic acid, camphorsulphonic acid and para-toluenesulphonic acid.

A cosolvent of $C_6$ to $C_{10}$ hydrocarbon type, for example cyclohexane or heptane, can also be added in the course of the process, in particular in a proportion of 1 equivalent by volume relative to the mass of the hydroxylated aromatic compound, or more generally in a ratio of from 0.5 to 3 equivalents.

The reaction can be carried out under a normal atmosphere. However, it is preferred to work under an inert gas atmosphere, for example, under nitrogen.

Moreover, the reaction may be carried out over a temperature range from 0 to 100° C., in particular from room temperature (about 25° C.) to about 70° C., preferably between 50 and 55° C. approximately, in particular in the case of the synthesis of 2,5-di-tert-octylhydroquinone.

The reaction is carried out at atmospheric pressure or at a higher pressure, the first case being preferred in particular when the olefinic compound is diisobutylene.

According to an advantageous embodiment of the invention, the hydroxybenzene, the catalyst, in particular a strong protonic acid, and the water + alcohol solvent are loaded with stirring and the mixture is preferably brought to the desired reaction temperature, after which the olefinic compound, the alcohol or the ether are run slowly into the mixture with stirring. More generally, the addition can be carried out over 0 to 72 hours.

The reaction time can vary as a function of the reaction conditions, in particular the temperature, and of the constituents, in particular the hydroxybenzene. It will generally range between 1 and 24 hours.

In a very advantageous manner, the products obtained, and in particular the 2,5-di-tert-octylhydroquinone, can precipitate in the reaction medium in accordance with the invention and can thus be recovered by simple separation methods, for example by filtration. It is thus not necessary to add the standard step of precipitation in water.

However, if necessary, the standard separation techniques can also be applied in order to recover the final product.

Another important advantage of the invention is that the mother liquors or filtrates can be recycled directly into the following operation.

One or more washes with water can also be carried out, preferably in the presence of a reducing agent such as sodium dithionite or sodium sulphite, in order to avoid oxidation phenomena.

The invention will now be described in greater detail with the aid of non-limiting exemplary embodiments.

EXAMPLE 1

In this example, 2,5-di-tert-octylhydroquinone is prepared.

110 g of hydroquinone (1 mol), 110 ml of water, 110 ml of methanol and 632 g of benzenesulphonic acid (4 mol) are introduced into a reactor. The mixture is heated to 55° C. with good stirring and under a stream of nitrogen. 560 g of diisobutylene (5 mol) are run in over 1 h 30, via an automated addition system. The reaction is then left to continue for 7 h. Next, the reaction medium is returned to room temperature. The 2,5-di-tert-octylhydroquinone precipitates out. The reaction medium is filtered and the precipitate is then washed with water. The dried precipitate is then recrystallized from n-hexane. A reaction yield of 74% di-tert-octylhydroquinone is obtained, for an 88% degree of conversion of the hydroquinone. The product is analysed and is given as >99% pure.

EXAMPLE 2

Synthesis via methanol: comparison

Same procedure, adding 220 ml of methanol instead of 110 ml of methanol +110 ml of water. A reaction yield of only 39% di-tert-octylhydroquinone is obtained, for an 80% degree of conversion of the hydroquinone.

EXAMPLE 3

Synthesis via water: comparison

Same procedure, adding 220 ml of water instead of 110 ml of methanol +110 ml of water.

A reaction yield of 25% di-tert-octylhydroquinone is obtained, for a 38% degree of conversion of the hydroquinone.

EXAMPLE 4

Synthesis of 2,5-di-tert-octylhydroquinone:

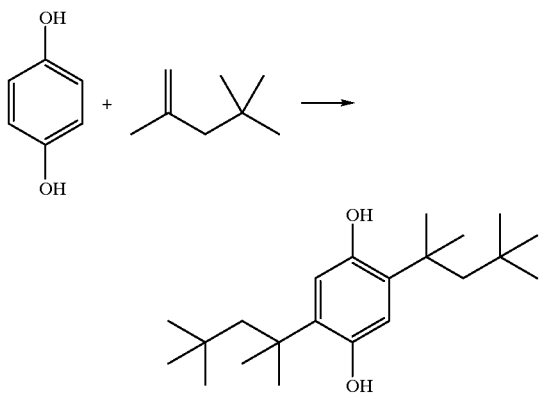

110 g of hydroquinone (1 mol), 110 ml of methanol, 110 ml of water and 632 g of benzenesulphonic acid (4 mol) are introduced into a reactor.

The mixture is heated to 55° C. with good stirring and under a stream of nitrogen. 561 g of diisobutylene (5 mol) are run in over 2 hours, via an automated addition system.

The reaction is then left to continue for 21 hours. The processing and purifications are identical to those above.

A reaction yield of 99% 2,5-di-tert-octylhydro- quinone is obtained, for a 99% degree of conversion of the hydroquinone.

EXAMPLE 5

Synthesis of Hexadecylhydroquinone

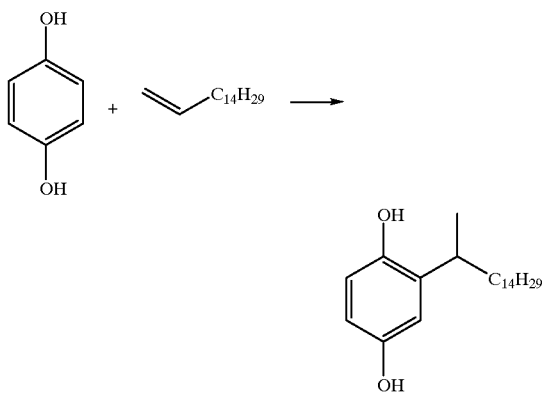

110 g of hydroquinone (1 mol), 110 ml of methanol, 110 ml of water and 632 g of benzenesulphonic acid (4 mol) are introduced into a reactor.

The mixture is heated to 100° C. with good stirring and under a stream of nitrogen.

1122 g of 1-hexadecene (5 mol) are run in over 2 hours, via an automated addition system.

The reaction is then left to continue for 18 hours.

The processing and purifications are identical to those above.

A reaction yield of 42% monohexadecylhydroquinone is obtained, for a 65% degree of conversion of the hydroquinone.

EXAMPLE 6

Synthesis of 3,5-di-tert-octylpyrocatechol

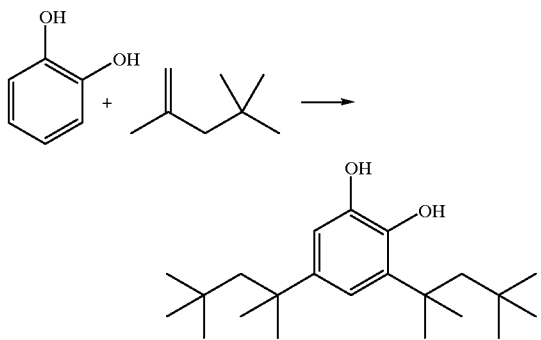

110 g of pyrocatechol (1 mol), 110 ml of methanol, 110 ml of water and 384 g of methanesuiphonic acid (4 mol) are introduced into a reactor.

The mixture is heated to 55° C. with good stirring and under a stream of nitrogen.

561 g of diisobutylene (5 mol) are run in over 2 hours, via an automated addition system.

The reaction is then left to continue for 5 hours.

The processing and purifications are identical to those above.

A reaction yield of 47% mono-tert-octylpyrocatechol and 5% 3,5-di-tert-octylpyrocatechol are obtained, for a 55% degree of conversion of the pyrocatechol.

EXAMPLE 7

Synthesis of 2,5-di-tert-butylhydroquinone

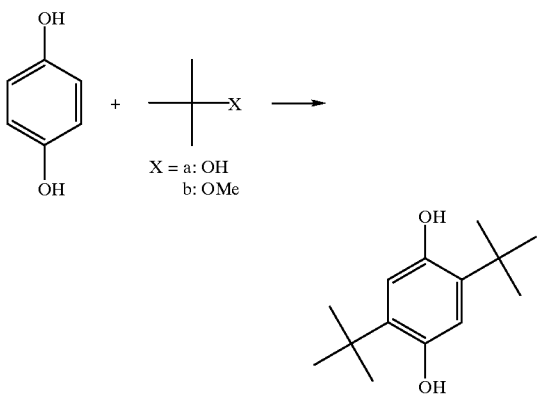

a: Use of tert-butanol 6.2 g of hydroquinone (0.056 mol), 6.2 ml of methanol, 6.2 ml of water and 35.4 g (0.224 mol, 4 eq.) of benzenesulphonic acid are introduced, under a stream of nitrogen, into a 250 ml reactor. The medium is brought to 55° C. and 20.9 g (0.282 mol, 5 eq.) of tertbutanol are added rapidly (5 min). After maintaining these conditions for 24 hours, the reaction medium is cooled to room temperature and processing and purification are carried out as above.

A yield of isolated product of 67.5% is obtained, for an 87% degree of conversion of the hydroquinone.

b: Use of methyl tert-butyl ether (MTBE)

12.4 g (0.113 mol) of hydroquinone, 49.8 g of MTBE (0.566 mol, 5 eq.) and 21.5 g (0.113 mol, 1 eq.) of 85% benzenesulphonic acid are introduced, under a stream of nitrogen, into a 250 ml reactor. The medium is then brought to 60° C. After maintaining these conditions for 5 hours, 25 ml of hexane are added and the reaction medium is cooled to 20° C. and then filtered in order to obtain 17.8 g of wet cake. This filter cake is placed in an oven (35° C.) under maximum vacuum for 12 h to give 14.6 g (58.3% yield for an 80% degree of conversion) of 2,5-di-tert-butylhydroquinone.

EXAMPLE 8

Synthesis of 3,5-di-tert-octylpyrocatechol

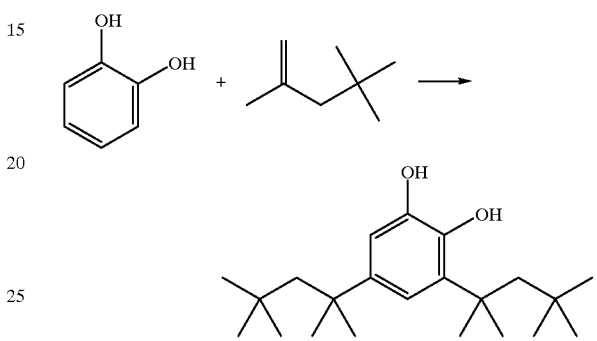

12.4 g of pyrocatechol (0.113 moi), 1.3 ml of methanol, 1.3 ml of water, 10 ml of cyclohexane and 2.2 [lacuna] (0.015 mol, 0.13 eq.) of triflic acid are introduced, under a stream of nitrogen, into a 250 ml reactor. After the medium has been brought to 55° C., 44 ml of diisobutylene (2.5 eq.) are added over 2 hours, using a dropping funnel. After maintaining these conditions for 19 hours, 24 ml of diisobutylene (1.36 eq.) are added over 2 hours and the medium is again maintained for 24 hours at 70° C.

A yield of product, assayed by HPLC (% of surface area) of 74% 3,5-di-tert-octylpyrocatechol and 23% of monoalkylation product are obtained, for a 99% degree of conversion of the pyrocatechol.

EXAMPLE 9

Synthesis of 2,5-di(1,1,2-trimethylpropyl)-hydroquinone

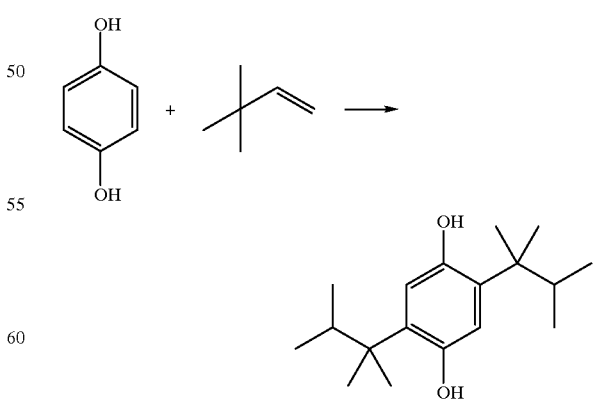

22 g of hydroquinone (0.2 mol), 5.5 ml of methanol, 5.5 ml of water and 31.54 g (0.2 mol, 1 eq.) of benzenesulphonic acid are introduced, under a stream of nitrogen, into a 250 ml reactor fitted with a condenser and a dropping funnel. After the medium has been brought to 50° C., 84.15 g of 3,3-dimethyl-1-butene (1 mol, 5 eq.) are added over 2 hours, using a dropping funnel.

After maintaining the alkene under reflux (boiling point= 41° C.) for 25 hours, the reaction medium is cooled to room temperature.

The dialkylation product is isolated by crystallization, adding 90 ml of a solution of methanol and water in a ratio of 2 to 1. The yield of isolated product is 37.2% for a 53% degree of conversion.

We claim:

1. Process for the C-alkylation of a hydroxylated aromatic compound having at least one hydrogen atom ortho or para to the hydroxyl group, in which process this aromatic compound is placed in the presence of a strong protonic acid and of a compound leading to the formation of a carbocation in the presence of the acid, the reaction being carried out in the presence of a solvent formed of a water/alcohol couple, wherein the water/alcohol ratio (as a % by volume) of the solvent is between 40/60 and 60/40.

2. Process according to claim 1, wherein the compound forming the carbocation in the presence of the acid is selected from the group consisting of:
   at least C3 olefinic compounds;
   secondary and tertiary alcohols; and
   ethers or amines having at least one secondary or tertiary group.

3. Process according to claim 1 wherein the hydroxylated aromatic compound has the formula:

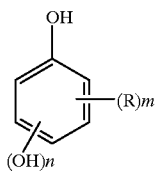

(1)

in which
   n=0 to 4,
   m=0 to 4,
   with n+m≦4
   R is chosen from the group consisting of:
      linear or branched C1 to C30 alkyl, which can optionally have one or more hetero atoms,
      one or more alkyls connected to the aromatic ring by a hetero atom, the alkyl corresponding to the above definition,
      a halogen atom,
   it being possible for 2 groups R placed on 2 adjacent carbon atoms to form, together with the atoms which bear them, 1 optionally substituted aromatic ring.

4. Process according to claim 1, wherein the alcohol of the solvent is a lower alcohol.

5. Process according to claim 4, wherein the alcohol of the solvent is selected from the group consisting of methanol, ethanol, isopropanol, cyclohexanol, ethylene glycol and a mixture of at least two of these.

6. Process according to claim 1, wherein the water+ alcohol solvent is used in a proportion of from 1 to 10 ml, per 1 g of acid.

7. Process according to claim 1, wherein the water+ alcohol/strong protonic acid ratio is between 1/0.1 and 1/10, expressed as volume/mass.

8. Process according to claim 1, wherein the strong protonic acid is a sulphonic acid.

9. Process according to claim 1, wherein the acid is chosen from the group consisting of sulphuric acid; halosulphonic acids, trifluoromethanesulphonic acid, methanesulphonic acid, ethanesulphonic acid, ethanedisulphonic acid, benzenesulphonic acid, benzenedisulphonic acid, toluenesulphonic acid, naphthalenesulphonic acid, naphthalenedisulphonic acid, camphorsulphonic acid, triflic acid and xylenesulphonic acid.

10. Process according to claim 1, wherein the strong protonic acid is used in a proportion of from 0.05 to 4 equivalents per 1 equivalent of the starting aromatic compound.

11. Process according to claim 1, wherein the olefinic compound is a linear or branched unsaturated aliphatic hydrocarbon containing at least one double bond.

12. Process according to claim 11, wherein the number of carbon atoms in the aliphatic hydrocarbon is between 3 and 30 carbon atoms.

13. Process according to claim 1, wherein the olefinic compound is an unsaturated, monocyclic or carbocyclic hydrocarbon or a polycyclic hydrocarbon comprising at least two carbocycles, it being possible for one or more hetero atoms to be present in the ring and at least one endocyclic or exocyclic unsaturation being present.

14. Process according to claim 1, wherein the olefinic compound is a terpenic compound.

15. Process according to claim 1, wherein the olefinic compound is used in a proportion of from 1 to 10 equivalents, per 1 equivalent of the starting aromatic compound.

16. Process according to claim 1, wherein the starting aromatic compound is hydroquinone.

17. Process according to claim 1, wherein the olefinic compound is diisobutylene.

18. Process according to claim 1, wherein the starting aromatic compound, the catalyst and the water+alcohol solvent are loaded with stirring, after which the olefinic compound is run into the mixture with stirring.

* * * * *